(12) United States Patent
Bari et al.

(10) Patent No.: US 10,769,181 B2
(45) Date of Patent: Sep. 8, 2020

(54) NOTIFICATION OF HEALTH EVENTS

(71) Applicant: AT&T Intellectual Property I, L.P., Atlanta, GA (US)

(72) Inventors: Farooq Bari, Kirkland, WA (US); Sankar Ray, Sammamish, WA (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 863 days.

(21) Appl. No.: 15/406,680

(22) Filed: Jan. 14, 2017

(65) Prior Publication Data
US 2017/0132249 A1 May 11, 2017

Related U.S. Application Data

(63) Continuation of application No. 13/053,667, filed on Mar. 22, 2011, now Pat. No. 9,582,839.

(51) Int. Cl.
| | |
|---|---|
| *G06F 16/29* | (2019.01) |
| *G06F 16/951* | (2019.01) |
| *G06Q 50/24* | (2012.01) |
| *G06Q 50/22* | (2018.01) |
| *H04L 29/06* | (2006.01) |

(52) U.S. Cl.
CPC .......... *G06F 16/29* (2019.01); *G06F 16/951* (2019.01); *G06Q 50/22* (2013.01); *G06Q 50/24* (2013.01); *H04L 67/42* (2013.01); *Y02A 90/22* (2018.01)

(58) Field of Classification Search
CPC .... G06Q 30/0261; G16H 10/60; G16H 20/17; G16H 40/63; G16H 50/30
See application file for complete search history.

(56) References Cited

U.S. PATENT DOCUMENTS

| | | |
|---|---|---|
| 6,463,273 B1 | 10/2002 | Day |
| 6,745,021 B1 | 6/2004 | Stevens |
| 7,389,104 B2 | 6/2008 | Phillips et al. |
| 7,725,565 B2 | 5/2010 | Li et al. |
| 7,752,259 B2 | 7/2010 | Weiser et al. |
| 7,808,378 B2 | 10/2010 | Hayden |
| 2003/0069002 A1 | 4/2003 | Hunter et al. |
| 2003/0163351 A1 | 8/2003 | Brown et al. |
| 2003/0220835 A1* | 11/2003 | Barnes, Jr. .......... G06F 3/04842 705/14.36 |
| 2004/0088374 A1 | 5/2004 | Webb et al. |
| 2005/0236474 A1 | 10/2005 | Onuma et al. |
| 2006/0036619 A1 | 2/2006 | Fuerst |
| 2006/0188073 A1 | 8/2006 | Wright |
| 2007/0222589 A1 | 9/2007 | Gorman et al. |
| 2008/0094228 A1 | 4/2008 | Welch et al. |
| 2008/0126960 A1 | 5/2008 | Naaman et al. |
| 2008/0133300 A1 | 6/2008 | Jalinous |
| 2008/0243863 A1 | 10/2008 | Kanaan |

(Continued)

*Primary Examiner* — Joseph D Burgess
(74) *Attorney, Agent, or Firm* — Scott P. Zimmerman, PLLC

(57) ABSTRACT

Methods, systems, and products notify of health events. Personal health information is stored in memory of a mobile communications device. A peer device is discovered through a wireless personal data network. The peer device is queried for anonymous health information. The anonymous health information is aggregated with the personal health information to produce aggregated health information. The aggregated health information is stored in the memory of the mobile communications device.

20 Claims, 16 Drawing Sheets

(56) References Cited

U.S. PATENT DOCUMENTS

| | | |
|---|---|---|
| 2009/0163170 A1 | 4/2009 | Norp et al. |
| 2009/0124232 A1 | 5/2009 | D'Arcy et al. |
| 2009/0164255 A1 | 6/2009 | Menschik et al. |
| 2009/0311986 A1 | 12/2009 | Bose et al. |
| 2010/0042429 A1 | 2/2010 | Dixit |
| 2010/0088107 A1 | 4/2010 | Ur et al. |
| 2010/0175006 A1 | 7/2010 | Li |
| 2010/0316196 A1 | 12/2010 | Jokinen |
| 2010/0318424 A1 | 12/2010 | LaValle |
| 2012/0116892 A1 | 5/2012 | Opdycke |

\* cited by examiner

NOTIFICATION OF HEALTH EVENTS

CROSS-REFERENCE TO RELATED APPLICATION

This application is a continuation of U.S. application Ser. No. 13/053,667 filed Mar. 22, 2011, since issued as U.S. Pat. No. 9,582,839, and incorporated herein by reference in its entirety.

BACKGROUND

Exemplary embodiments generally relate to telecommunications, to electrical computers, to data processing, and to communications and, more particularly, to emergency communications, to location monitoring, to health care management, and to database and file access.

Allergens, communicable diseases, and other health-related incidences are increasingly important in today's global environment. Global commerce and travel have increased our exposure to harmful biological organisms. People need to be alerted when conditions may impact their health and well-being.

BRIEF DESCRIPTION OF THE SEVERAL VIEWS OF THE DRAWINGS

The features, aspects, and advantages of the exemplary embodiments are better understood when the following Detailed Description is read with reference to the accompanying drawings, wherein.

DETAILED DESCRIPTION

The exemplary embodiments will now be described more fully hereinafter with reference to the accompanying drawings. The exemplary embodiments may, however, be embodied in many different forms and should not be construed as limited to the embodiments set forth herein. These embodiments are provided so that this disclosure will be thorough and complete and will fully convey the exemplary embodiments to those of ordinary skill in the art. Moreover, all statements herein reciting embodiments, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and the like represent conceptual views or processes illustrating the exemplary embodiments. The functions of the various elements shown in the figures may be provided through the use of dedicated hardware as well as hardware capable of executing associated software. Those of ordinary skill in the art further understand that the exemplary hardware, software, processes, methods, and/or operating systems described herein are for illustrative purposes and, thus, are not intended to be limited to any particular named manufacturer.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will also be understood that, although the terms first, second, etc. may be used herein to describe various elements, these elements should not be limited by these terms. These terms are only used to distinguish one element from another. For example, a first device could be termed a second device, and, similarly, a second device could be termed a first device without departing from the teachings of the disclosure.

Figure 1:
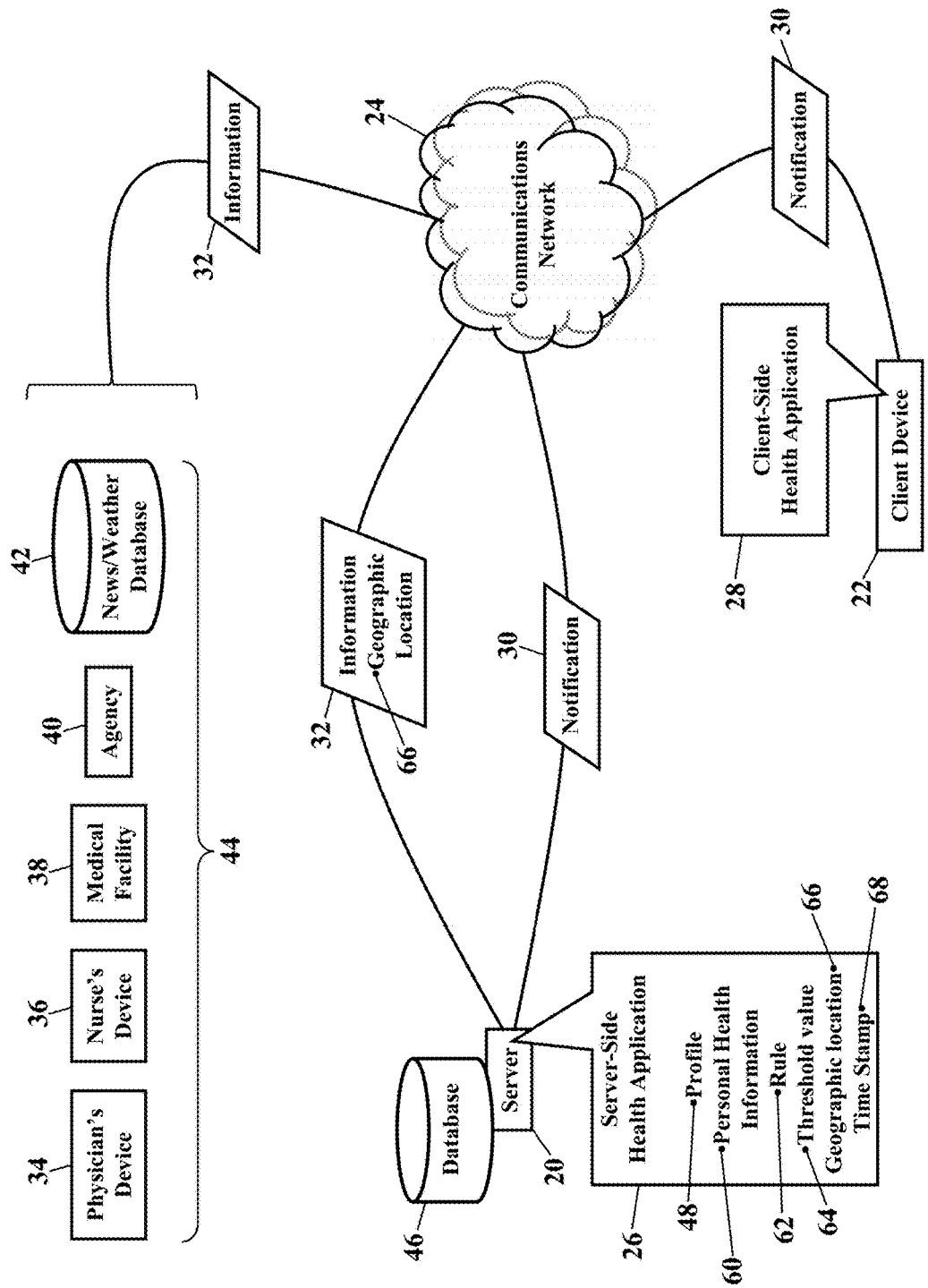
FIG. 1 is a simplified schematic illustrating an environment in which exemplary embodiments may be implemented.

FIG. 1 is a simplified schematic illustrating an environment in which exemplary embodiments may be implemented. FIG. 1 illustrates a client-server network architecture that provides notifications of health events. A server 20 communicates with a client device 22 via a communications network 24. The server 20 executes a server-side health application 26, while the client device 22 executes a client-side health application 28. The server-side health application 26 and the client-side health application 28 comprise software code or instructions that cooperate in a client-server fashion to send a notification 30 to the client device 22. The server 20 receives all kinds of information 32 that may be used to discern health events of interest. The server 20, for example, may receive the information 32 from a physician's device 34, a nurse's device 36, a medical facility 38 (such as a hospital or doctor's office), government agency 40, and/or a news and weather database 42. The server 20 stores the information 32 from these various sources 44 in a database 46. The database 46 is illustrated as being locally stored in the server 20, but the database 46 may be remotely maintained and accessed from some location in the communications network 24. Regardless, the server-side health application 26 compares the information 32 in the database 46 to a health profile 48. If any of the information 32 matches or satisfies the health profile 48, then the server-side health application 26 may send the notification 30. The notification 30 communicates via the communications network 24 to some destination (such as the client device 22). The notification 30 may be an email, text message, call, or any electronic or audible message. The notification 30 informs the user of the client device 22 of the information 32 in the database 46 that matches the health profile 48.

The health profile 48 stores personal health information 60 related to the user of the client device 22. The personal health information 60, for example, may include allergens, illnesses, and other medical concerns. The personal health information 60 may include blood type, height, weight, medical history, and even DNA/RNA markers. The personal health information 60 may include prescription medications and over-the-counter medications previously or currently taken by the user. The personal health information 60, however, may also include alcohol consumption and even illicit or illegal drugs previously or currently taken by the user. The personal health information 60 may include dietary habits, dietary restrictions, and physical limitations. The personal health information 60 may also include mental health parameters. The health profile 48, in short, stores any personal health information 60 that may help discern health events of interest to the user.

The health profile 48 may also store one or more rules 62 and threshold values 64. Each rule 62 logically expresses some key word or subject matter which is compared to the information 32 in the database 46 and/or to the personal health information 60 in the health profile 48. Each threshold value 64 represents some maximum, minimum, or range of parameter values for which the notification 30 is desired. When any threshold value 64 is equaled or exceeded, the corresponding rule 62 causes the health application 26 to send the notification 30. The health profile 48 may thus be configured to alert of any information 32 in the database 46, and/or any personal health information 60 in the health profile 48, that may affect or impair the personal health of the user.

Exemplary embodiments also utilize a geographic location 66 associated with each health event. As the server 20 collects the information 32 from the various sources 44, the server-side health application 26 also receives the geographic location 66 associated with each report or data. The geographic location 66, for example, may be global positioning system (GPS) coordinates. Many computers, smart phones, and other devices have GPS capability, so the geographic location 66 is added or appended to any reports. When the server-side health application 26 receives the source information 32, then the server-side health application 26 also knows the geographic location 66 associated with the health event. When the reported health event is stored in the database 46, the database 46 may also associate the reported health event to the geographic location 66 (e.g., the GPS location coordinates). Later paragraphs will further explain automatic location-based reporting of health events.

FIG. 1 also illustrates automatic time-based reporting of health events, according to exemplary embodiments. Here each health event is also time stamped to indicate a date and time. As FIG. 1 illustrates, the server-side health application 26 adds a time stamp 68 to each health event reported by the source information 32. As the server-side health application 26 receives the source information 32, the server-side health application 26 thus also knows the date and time associated with the health event. The server 20 stores the reported health event in the database 46, along with the time stamp 68. Exemplary embodiments thus also permit automatic time and date reporting of health events. Later paragraphs will further explain the time stamp 130.

Exemplary embodiments may be explained using airborne pollen. Suppose the user of the client device is allergic to oak spores, ragweed, or any other generally-termed "pollen." The user may wish to be informed of daily ambient conditions in some location that exceed a predefined pollen count. The user, then, configures the health profile 48 with the rule 62 that describes the threshold value 64 of pollen counts in the geographic location 66 for which notification is desired. If the database 46 receives and stores pollen counts as a data feed from a source (such as a weather feed from a weather-related website or database), then the server-side health application 26 may compare the daily pollen count (associated with the geographic location 66) to the threshold value 64 of pollen counts. If the daily pollen count for the geographic location 66 equals or exceeds the threshold value 64, then the server-side health application 26 may send the notification 30. The notification 30 alerts the user of high pollen counts.

The health profile 48 may store many other health factors and parameters. The health profile 48, for example, may store the rules 62 describing temperature or other weather conditions for which the notification 30 is desired. The health profile 48, however, may also store the rules 62 describing any parameters for which the notification 30 is desired. The user, for example, may be concerned about e-coli, malaria, influenza, or any other infectious disease or exposure. The user may thus configure the rules 62 to require the notification 30 when any transmissible disease, or any other health event, is reported. The health profile 48, in other words, may store the configurable rules 62 and threshold values 64 for any health factors, parameters, or conditions which may be logically expressed.

The health profile 48 may even store food and shopping information. The health profile 48, for example, may store food items that are purchased, such as brands of peanut butter, milk, vegetables, and any other items. The rules 62 may then be configured to send the notification 30 when the sources 44 indicate a food item poses a health concern. Suppose, for example, that the source information 32 indicates a nationally-recognized brand of peanut butter is being recalled due to salmonella exposure. If the health profile 48 has an entry that matches the same brand of peanut butter, then the rules 62 may require that the notification 30 be sent to alert of the salmonella exposure in the peanut butter. The health profile 48, likewise, may store names and addresses of grocers, retailers, and other establishments. If the source information 32 indicates any establishment issues a product recall, then exemplary embodiments may compare the health profile 48 to the source information 32. When an entry that matches, then the rules 62 may send the notification 30 to alert of the recall.

The health profile 48 may store rules 62 and the thresholds 64 for multiple people. The health profile 48, for example, may contain the personal health information 60 for a family (such as mother, father, and children). Different rules 62 and thresholds 64 may be established for each member of the family. The health profile 48, however, may be configured for other groups, such as teams, workers, and roommates. The health profile 48 may also be configured for individuals.

Figure 2:
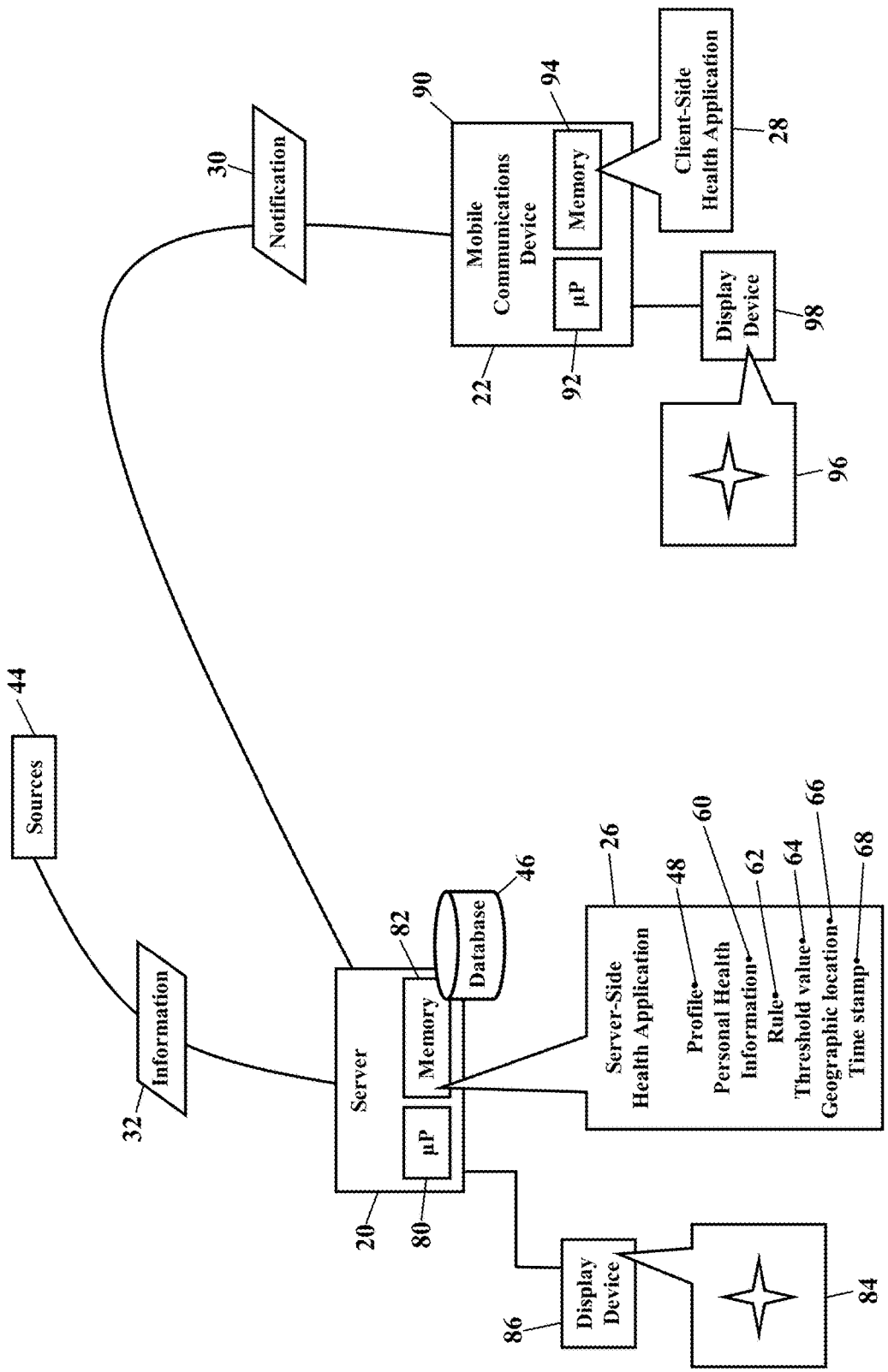
FIG. 2 is a more detailed schematic illustrating the operating environment, according to exemplary embodiments.

FIG. 2 is a more detailed schematic illustrating the operating environment, according to exemplary embodiments. The server 20 has a processor 80 (e.g., "µP"), application specific integrated circuit (ASIC), or other component that executes the server-side health application 26 stored in a memory 82. The health application 26 may cause the processor 80 to produce a graphical user interface ("GUI") 84. The graphical user interface 84 is illustrated as being visually produced on a display device 86, yet the graphical user interface 84 may also have audible features. The server-side health application 26, however, may operate in any processor-controlled device, as later paragraphs will explain.

FIG. 2 also illustrates the client device 22. The client device 22 is illustrated as a mobile communications device 90, such as a cellular phone, notebook computer, tablet computer, IPAD®, or other portable communications device. The client device 22 also has a processor 92 (e.g., "µP"), application specific integrated circuit (ASIC), or other component that executes the client-side health application 26 stored in a memory 94. The client-side health application 26 may cause the processor 92 to produce a graphical user interface ("GUI") 96 on a display device 98 of the client device 22. The client-side health application 28, however, may also operate in any processor-controlled device, as later paragraphs will explain.

The server-side health application 26 and the client-side health application 28 cooperate. The server 20 receives the information 32 from the sources 44 and stores the information 32, the geographic location 66, and the time stamp 68 in the database 46. The server-side health application 26 compares the information 32 in the database 46 to the health profile 48. The health profile 48 stores the personal health information 60, rules 62, and threshold values 64 associated with one or more persons. If any of the information 32 in the database 46 matches and/or satisfies the personal health information 60, the rules 62, and/or the threshold values 64, then the server-side health application 26 sends the notification 30.

FIGS. 1 and 2, for simplicity, only illustrate a single client-side health application 28. FIGS. 1 and 2 illustrate the single client-side health application 28 that is executed by the client device 22. Using conventional nomenclature, though, the sources 44 may also be considered as "clients" to the server 20. The various sources 44 (illustrated in FIG. 1) also execute a client application that reports the source information 32 to the database 46. This disclosure, though, is focused on the client device 22, so FIGS. 1 and 2 only illustrate the client-side health application 28 that is executed by the client device 22.

Figure 3:
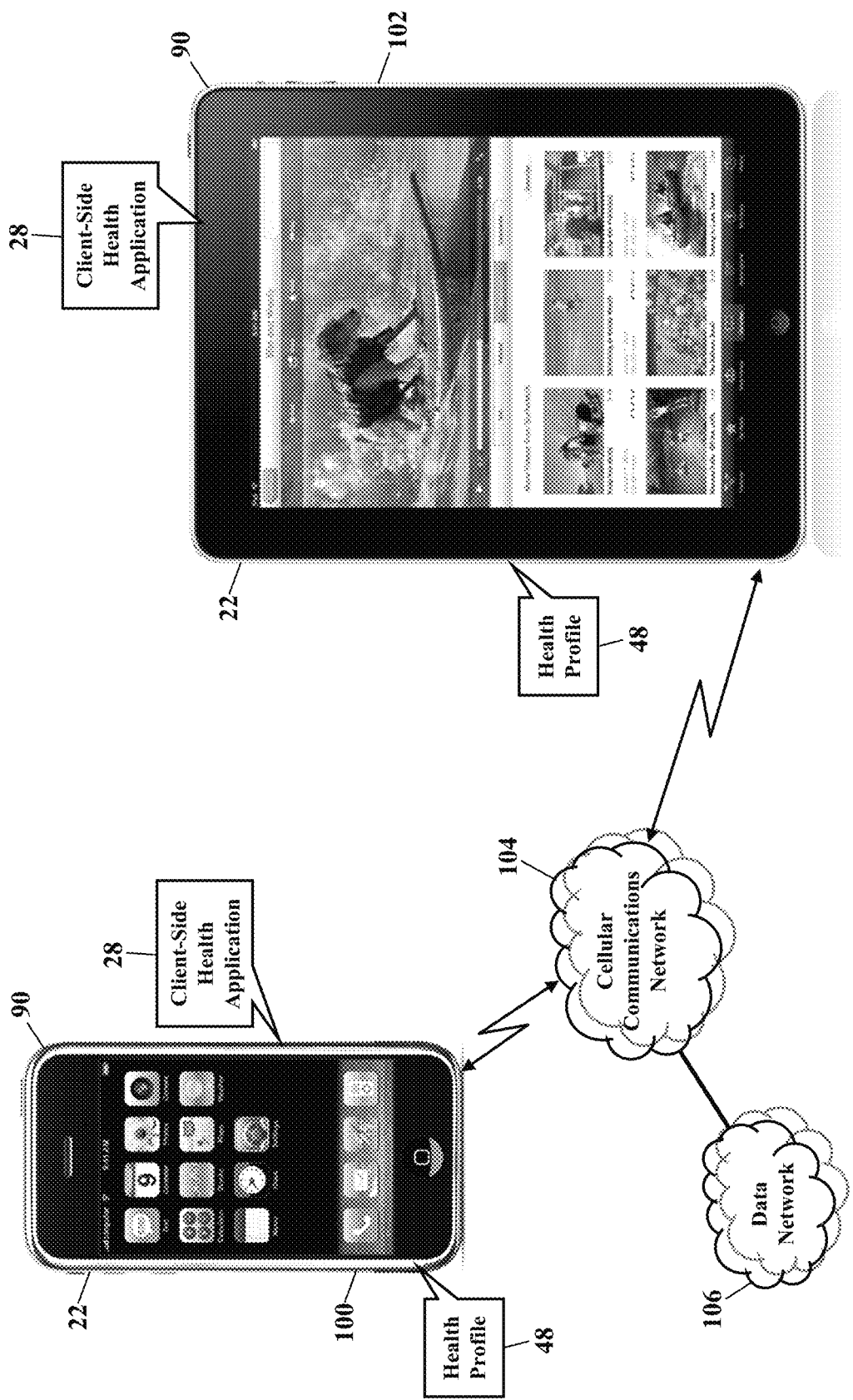
FIG. 3 is a schematic illustrating a client device, according to exemplary embodiments.

FIG. 3 is a schematic further illustrating the client device 22, according to exemplary embodiments. FIG. 3 illustrates the client device 22 as the mobile communications device 90, such as a smart phone 100 or a tablet computer 102 (such as Apple's IPAD®). FIG. 3 also illustrates that the client device 22 may communicate with a cellular communications network 104. The cellular communications network 104 may itself communicate or interface with a data network 106. The mobile communications device 90 may download the client-side health application 28 via the data network 106 (such as from an online application store). Exemplary embodiments thus include a publically-available smart phone or cell phone application that receives the notification of health events from the server (illustrated, respectively, as reference numeral 30 and 20 in FIGS. 1 and 2). The notification 30 may be an email, text message, voice-over Internet Protocol call, or any electronic notification. Because the mobile communications device 90 also communicates with the cellular communications network 104, the notification 30 may also be a telephone call.

Figure 4:
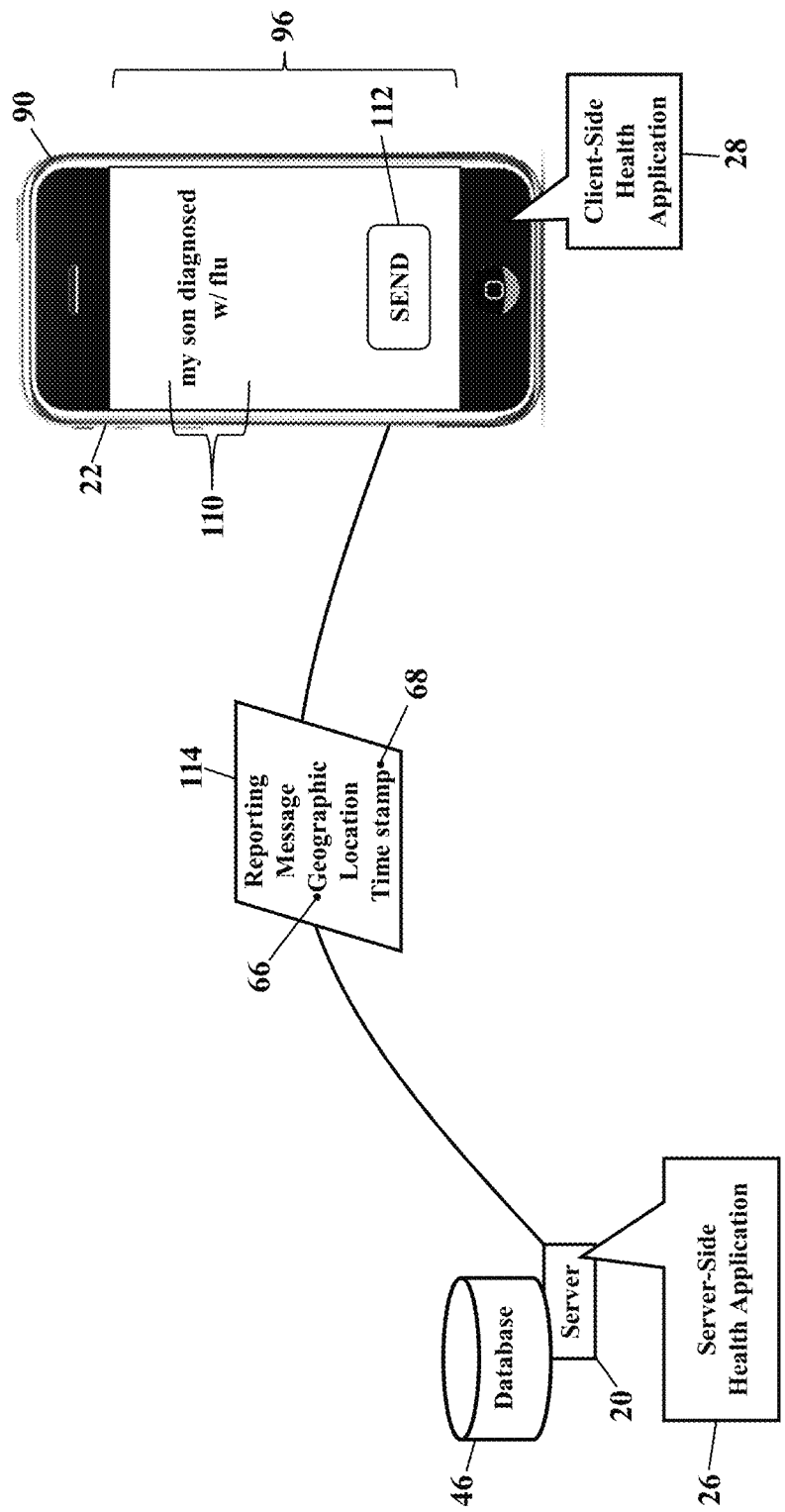
FIG. 4 is a schematic illustrating reporting of health events, according to exemplary embodiments.

FIG. 4 is a schematic illustrating reporting of health events, according to exemplary embodiments. Here the client-side health application 28 may be used to report health events to the server 20. The user of the client device 22 may wish to report an instance of influenza, pneumonia, salmonella, or other infectious concern. The user of the client device 22 may hope that reporting these micro-instances of health events helps reduce infection rates in other people. As FIG. 4 illustrates, then, a good-health Samaritan may use the client-side health application 28 to report individual health events. The graphical user interface 96 produced by the client-side health application 28 may include a text field 110. The user places a cursor in the text field 110 and types a textual description of the health event (e.g., "my son diagnosed with flu"). The user performs some authorization (such as selecting a "SEND" graphical control 112), and the client-side health application 28 then causes a reporting message 114 to be sent. The reporting message 114 includes the text entered into the text field 110. The reporting message 114 also includes the geographic location 66 and the time stamp 68. The geographic location 66 describes the location sensed by the client device 22, and the time stamp 68 represents the date and time of the reported event. The reporting message 114 communicates to an address associated with the server 20. When the server 20 receives the reporting message 114, the server-side health application 26 may parse and store the text as an entry in the database 46. The server-side health application 26 may then use this micro-report to notify others of the event reported by the user of the client device 22. Here, then, the user directly contributes to public health efforts to reduce the spread of infectious diseases.

Figure 5:
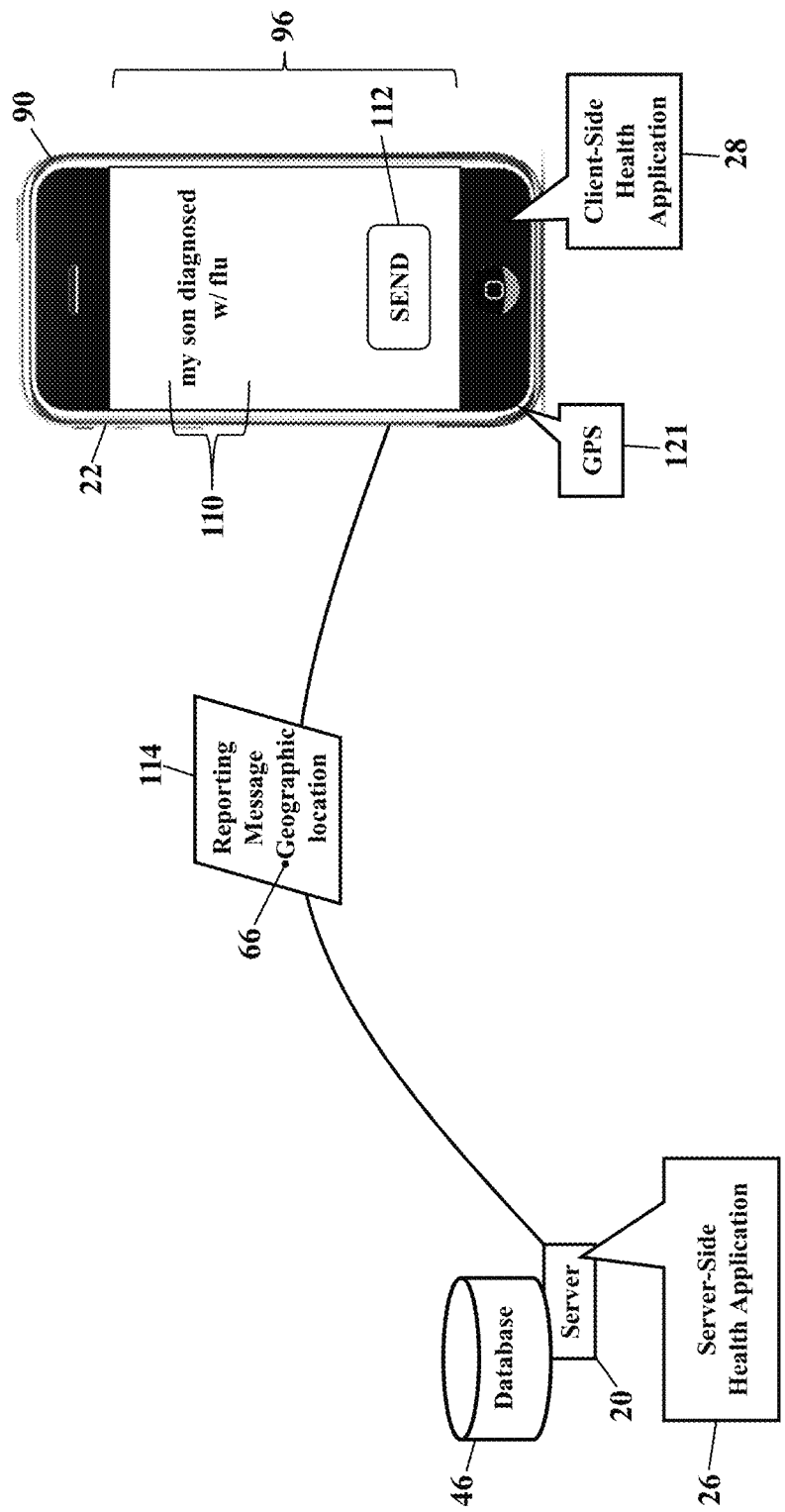
FIGS. 5-7 are schematics illustrating location reporting of health events, according to exemplary embodiments.
Figure 6:
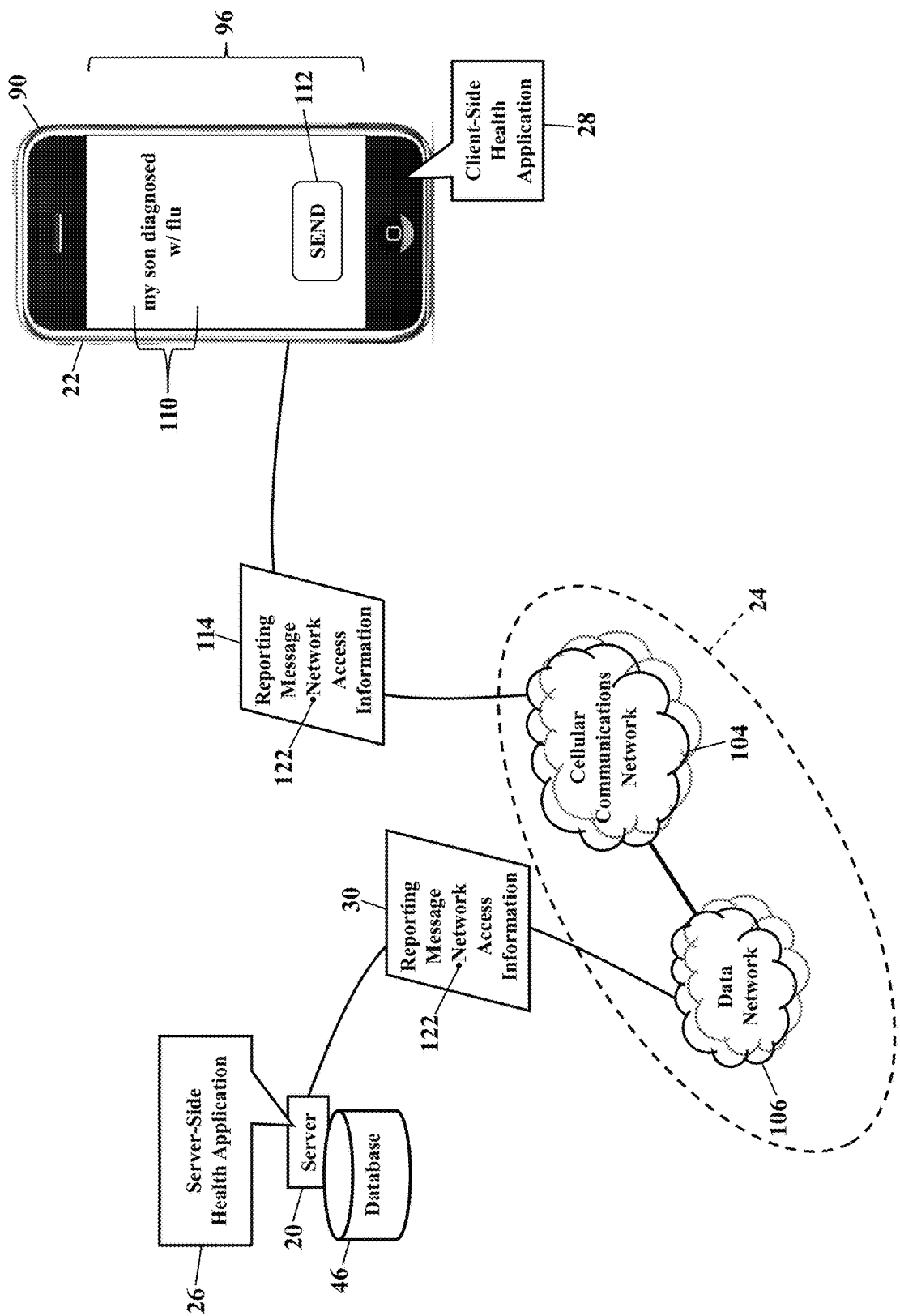
Figure 7:
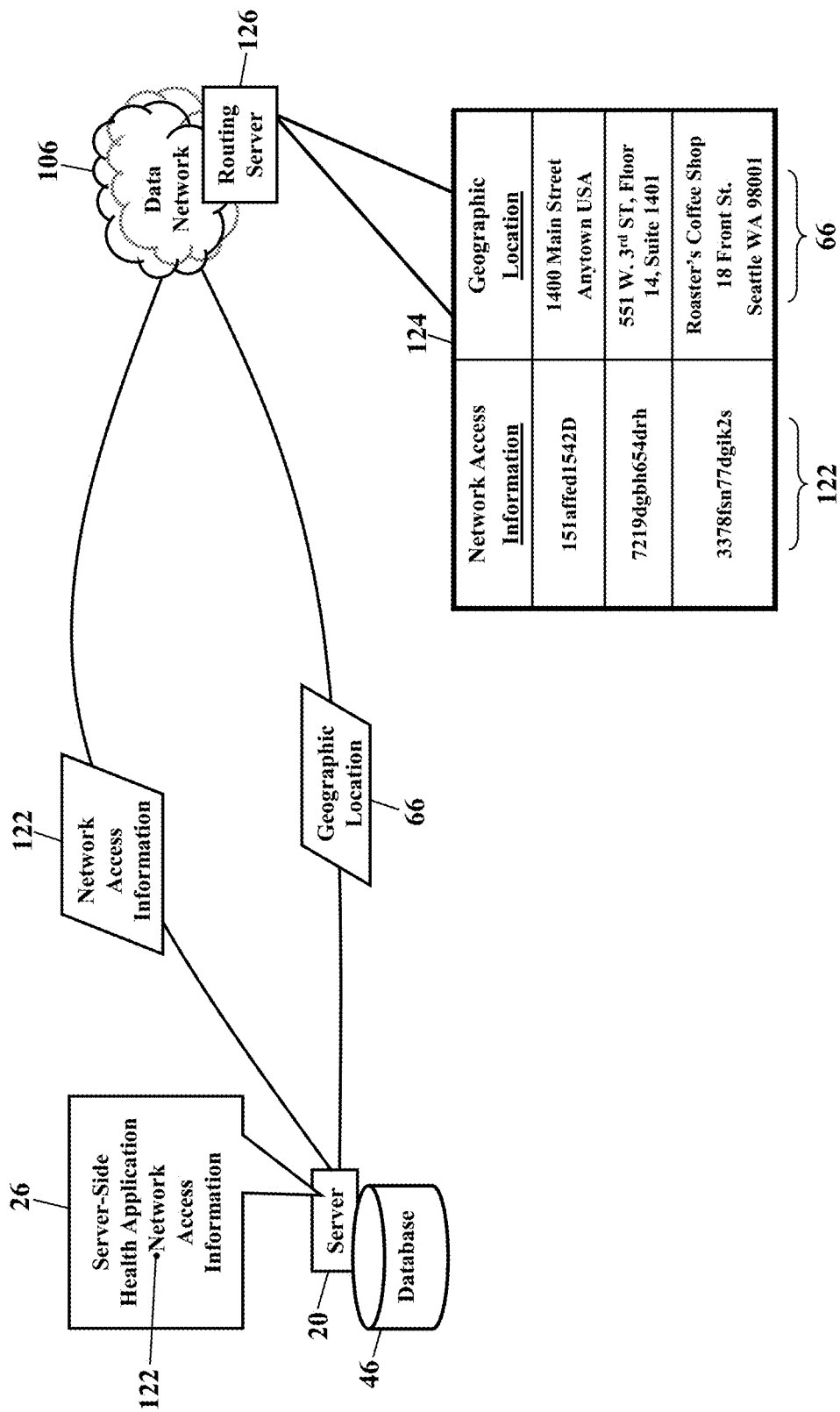

FIGS. 5-7 are schematics further illustrating location reporting of health events, according to exemplary embodiments. Here the client-side health application 28 automatically reports the geographic location 66 associated with health events. When the user of the client device 22 wishes to report some health event (such as the instance of influenza described above with reference to FIG. 4), the client-side health application 28 sends the reporting message 114 to the server 20. Here, though, the geographic location 66 is added to the reporting message 114 (such as a header or payload of the reporting message 114). As FIG. 5 illustrates, the geographic location 66 may be global positioning system (GPS) coordinates from a GPS component 121 in the client device 22. Because many computers, smart phones, and other devices have GPS capability, the client-side health application 28 may add or append GPS location coordinates to the reporting message 114. When the server 20 receives the reporting message 114, then server-side health application 26 also knows the geographic location 66 associated with the health event. When the reported health event is stored in the database 46, the database 46 also associates the reported health event to the geographic location 66 (e.g., the GPS location coordinates). Exemplary embodiments thus permit automatic location-based reporting of health events from the client device 22.

FIG. 6, though, illustrates network access information 122. There may be times when global positioning system (GPS) coordinates are not available and/or not adequately descriptive of the geographic location 66 of the client device 22. GPS coordinates, for example, do not distinguish between indoor and outdoor locations. Often times health events are more meaningful if known to occur indoors or outdoors. Moreover, indoor locations often cannot receive signals from GPS satellites.

FIG. 6, then, illustrates the network access information 122. When the user of the client device 22 wishes to report some health event, the client-side health application 28 sends the reporting message 114. Here, though, the reporting message 114 includes the network access information 122. The network access information 122 describes an access point to the communications network 24. The network access information 122, for example, may uniquely describe a cellular antenna, base station, or access point of the cellular communications network 104 that communicates with the client device 22. The network access information 122 may additionally or alternatively describe a wireless WI-FI® router of the data network 106 that communicates with the client device 22. Whatever the network access point, each network access point may have a unique alphanumeric identification number. This unique alphanumeric identification number may be appended or added to the reporting message 114 (such as a header or payload). The network access information 122 may be added by the client-side health application 28 when the reporting message 114 is sent, or the network access information 122 may be added to the reporting message 114 by the access point. When the server 20 receives the reporting message 114, then server-side health application 26 may also know the network access information 122 associated with the health event.

FIG. 7 illustrates further illustrates the network access information 122. Once the network access information 122 is known, the server-side health application 26 may then determine the geographic location 66 of the reported health event. As FIG. 7 illustrates, the server-side health application 26 may then consult a table 124. The table 124 is illustrated as being remotely stored in memory of a routing server 126, but the table 124 may be locally stored in the memory of the server 20. The table 124 stores entries that associate the network access information 122 to the geographic location 66. The table 124 stores a more detailed description of the geographic location 120 associated with the network access information 122. The table 124, for example, may store a street address, building, floor or other identifier associated with the network access information 122. The server-side health application 26 queries the routing server 126 for the network access information 122. The routing server 126 retrieves and responds with the corresponding geographic location 66. The server 20 stores the reported health event in the database 46, along with the geographic location 66 associated with the network access information 122. Exemplary embodiments thus permit automatic location-based reporting of health events from the client device 22.

Figure 8:
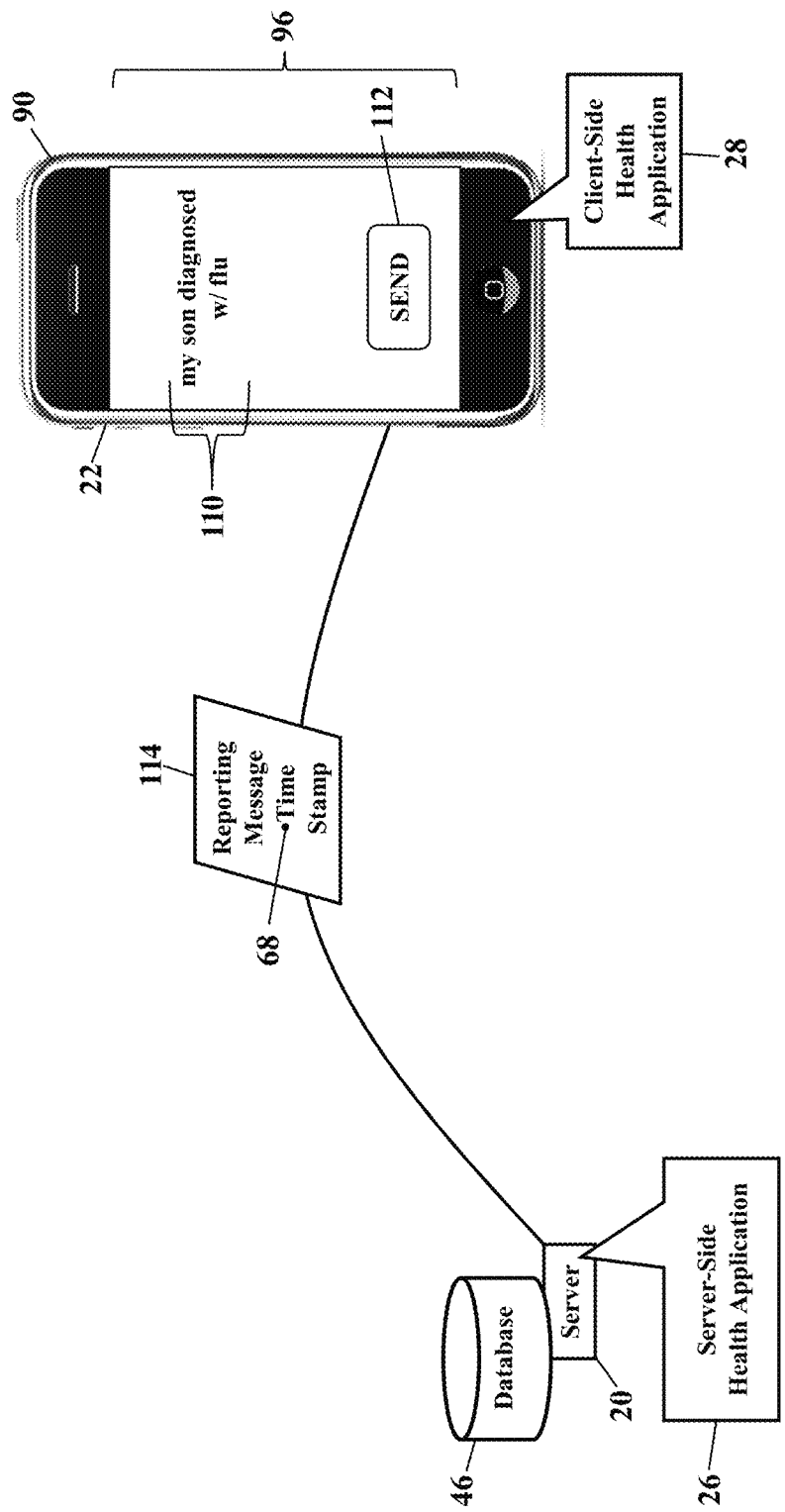
FIG. 8 is a schematic illustrating a time stamp, according to exemplary embodiments.

FIG. 8 is another schematic further illustrating the time stamp 68, according to exemplary embodiments. Here the client-side health application 28 adds the time stamp 68 to each health event reported by the client device 22. When the client device 22 sends the reporting message 114, the client-side health application 28 adds or appends the time stamp 68 to a header or payload of the reporting message 114. When the server 20 receives the reporting message 114, the server-side health application 26 then knows the time and date associated with the health event. The server 20 stores the reported health event in the database 46, along with the time stamp 68. Exemplary embodiments thus also permit automatic time and date reporting of health events from the client device 22.

Figure 9:
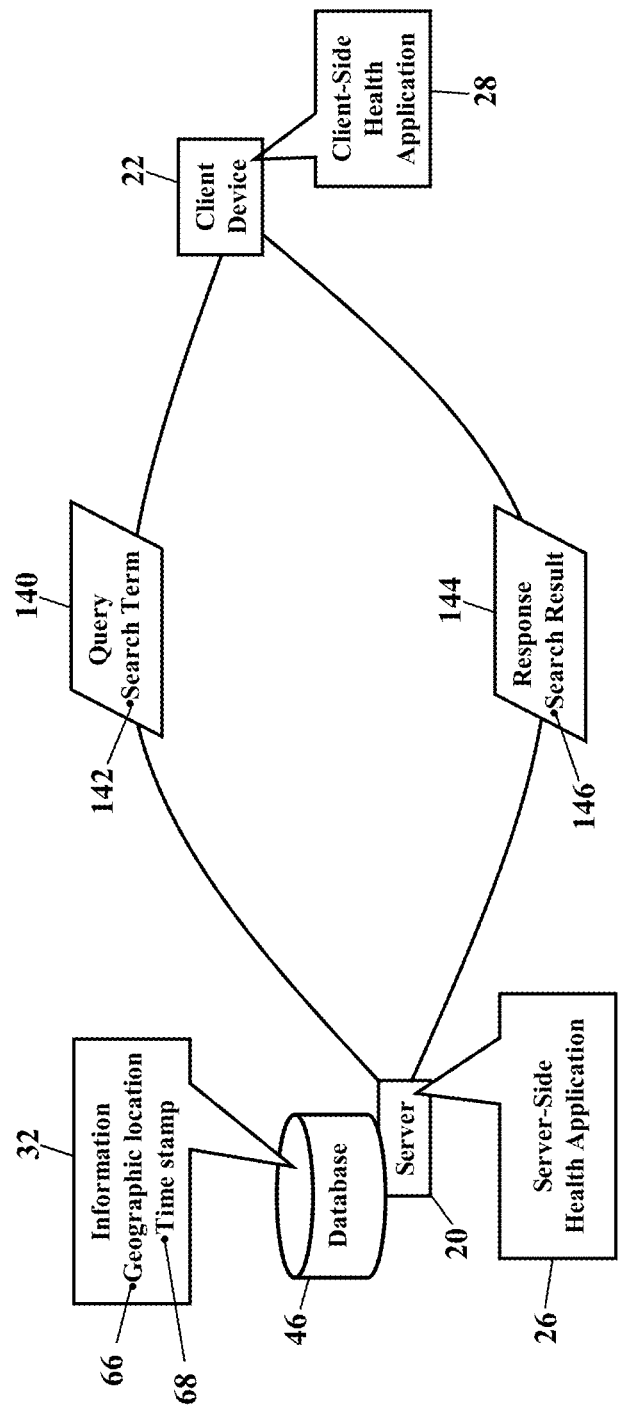
FIG. 9 is a schematic illustrating database queries, according to exemplary embodiments.

FIG. 9 is a schematic illustrating database queries, according to exemplary embodiments. As more and more physicians, agencies, and even individual members of the public report health events, the database 46 builds a comprehensive, centralized repository of the information 32. Moreover, the information 32 stored in the database 46 is automatically associated with the geographic location 66 and with the time stamp 68. The database 46 thus stores a wealth of information that may be queried for keywords, location, and/or time. FIG. 9, then, illustrates a query 140 to the database 46. The query 140 may originate from any device. For simplicity, though, FIG. 9 illustrates the query 140 originating from the client device 22. The query 140 includes a search term 142, and the query 140 routes through the communications network (illustrated as reference numeral 24 in FIG. 1) to the address associated with the server 20. When the server 20 receives the query 140, the server-side health application 26 queries the database 46 for the search term 142. The server 20 then sends a response 144, and the response 144 includes a search result 146. The query 140 routes through the communications network 24 to an address associated with the client device 22. So, not only do exemplary embodiments provide automatic notification of health events, but exemplary embodiments also permit queries from physicians, nurses, agencies, and even individual members of the public.

An example helps explain the query 140. Suppose the client device 22 is the mobile communications device 90, and the mobile communications device 90 travels from New York City to Paris, France. Upon arrival in Paris, the user may wish to know of any health concerns while visiting Paris. The user, then, commands or instructs the client-side health application 28 to send the query 140 with "Paris France" as the search term 142. When the server 20 receives the query 140, the server-side health application 26 queries the database 46 for "Paris France" and sends the search result 146 to the client device 22. The user may thus review the search result 146 to learn of health events associated with Paris, France. Moreover, because the client device 22 is currently located in Paris, the server-side health application 26 may "push" the notification 30 to the client device 22 when Paris-related information is determined. The client-side health application 28 may even be configured to periodically "pull" or issue the query 140 for updated health events for Paris.

The database 46 may even be queried for symptoms. The user may be suffering from an unknown illness. The user, then, may then send the query 140 with a description of the symptoms as the search term 142. When the server 20 receives the query 140, the server-side health application 26 queries the database 46 for a textual description of the symptoms and sends the search result 146 to the client device 22. The user may thus review the search result 146 to diagnose the symptoms.

Exemplary embodiments may also include privacy settings. When the client device 22 communicates with the server 20, reports of individual health events may be partially, or completely, anonymous. Medical laws may prevent or prohibit disclosure of personal information. Moreover, even though individual members of the public may report their own health events, most people would prefer that those reports not include personal information. Exemplary embodiments, then, may partially or completely anonymize reports of health events. The client-side health application 28, for example, may have configuration settings that prohibit certain data fields from being sent. A name and home address of the user of the client device 22, for example, may be prohibited from being retrieved and sent with the reporting message 114. Names and addresses family members may also be prohibited. Configuration settings may even be established to ensure certain information (such as ailments, diseases, or medications) are not revealed.

Figure 10:
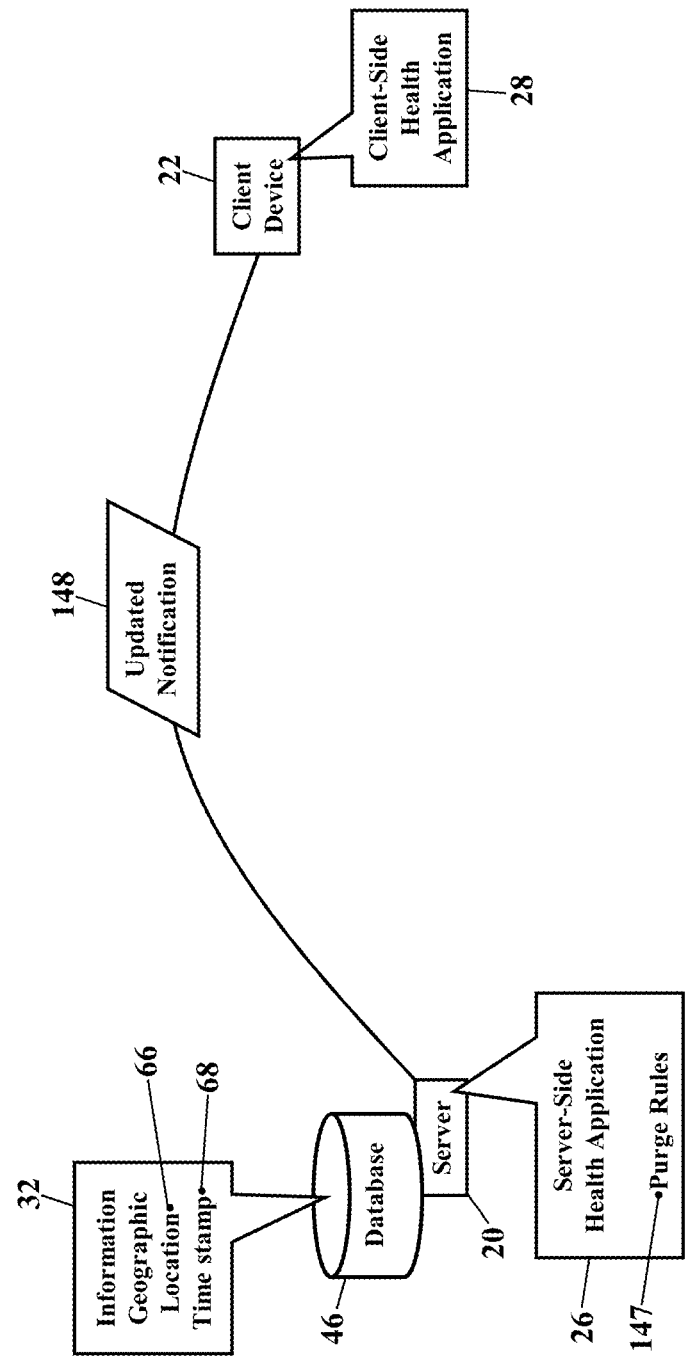
FIG. 10 is a schematic illustrating purging of a database, according to exemplary embodiments.

FIG. 10 is a schematic illustrating purging of the database 46, according to exemplary embodiments. As the above paragraphs explained, over time the database 46 builds a comprehensive, centralized repository of the information 32. As time passes, however, some of the information 32 may become stale and/or no longer useful. A report of influenza, for example, is perhaps no longer relevant after six months. Moreover, the larger the database 46 becomes, the slower the database 46 responds to queries. Exemplary embodiments, then, may purge data from the database 46. FIG. 10 illustrates purge rules 147 that determine what information 32 is deleted or purged from the database 46. The purge rules 147, for example, may compare the information 32 in the database 46 to a threshold age. If the time stamp 68 associated with an entry in the database 46 exceeds the threshold age, then the purge rules 147 may instruct the server-side health application 26 to delete the entry. Likewise, exemplary embodiments may compare the geographic location 66 to a threshold location (such as a radius about a GPS coordinate or postal ZIP code). If the geographic location 66 associated with an entry in the database 46 exceeds the threshold location, then the purge rules 147 may instruct the server-side health application 26 to delete the associated entry. The purge rules 147 thus ensure that the information 32 stored in the database 46 remains relevant.

FIG. 10 also illustrates updated notifications, according to exemplary embodiments. When information is purged from the database 46, the information is, implicitly, no longer considered a concern. The purged information, in other words, is too old or too geographically remote to require reporting. Exemplary embodiments, then, may notify users that the purged information is no longer a concern. Suppose that notifications were sent to warn of influenza in the Seattle, Wash. area. After six months, though, the risk of exposure may be low, so the reports are purged from the database 46. Because influenza is no longer a concern, the residents of Seattle may be notified that influenza is no longer a risk. FIG. 10, then, illustrates an updated notification 148. When information is purged from the database 46, the server-side health application 26 may send the updated notification 148. The updated notification 148 describes the health event that is no longer of concern and that will be purged from the database 46. Even though the health event is purged from the database 46, sensible management may archive the health event in long-term storage (not illustrated).

Figure 11:
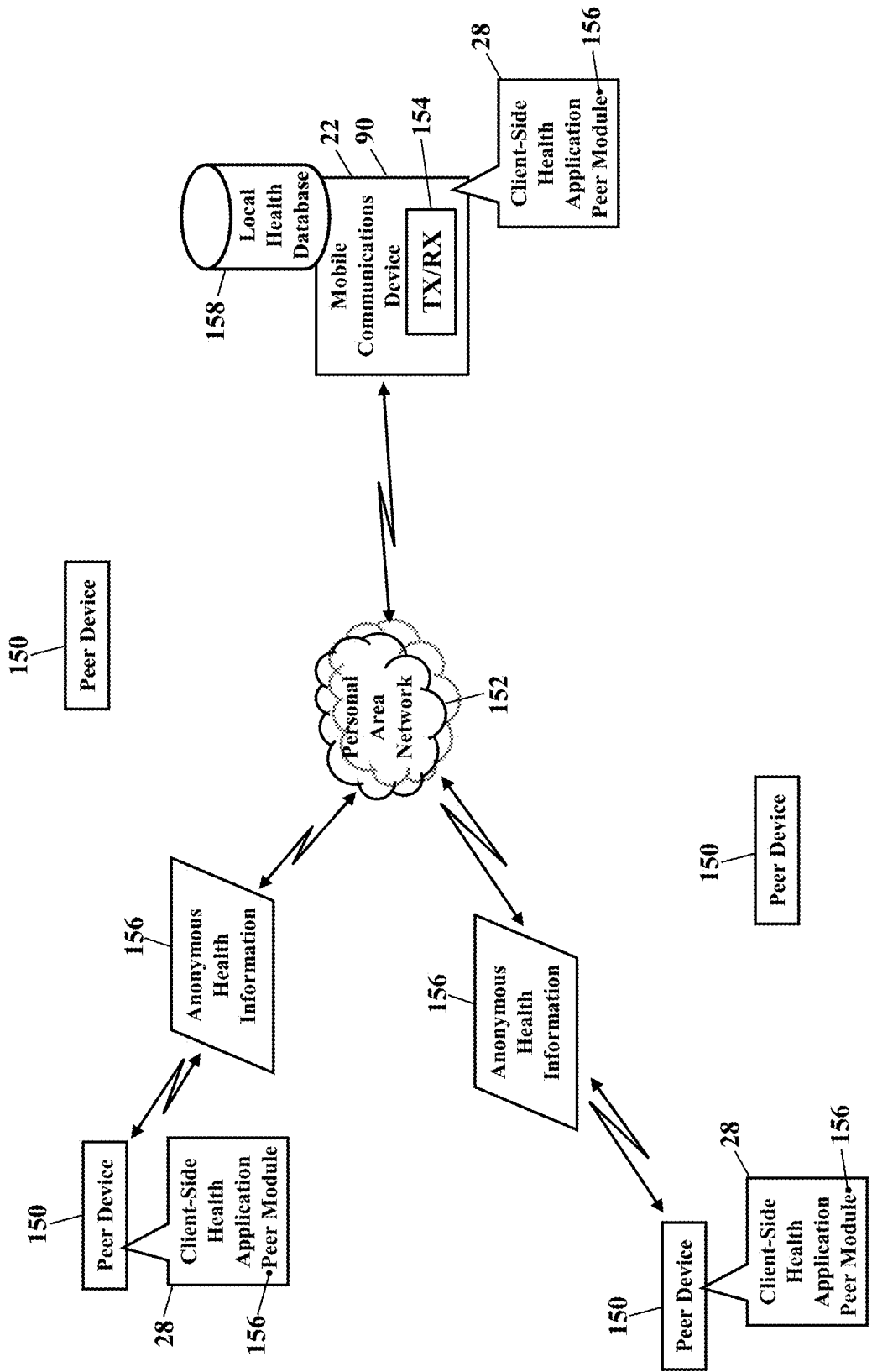
FIG. 11 is a schematic illustrating peer networks, according to exemplary embodiments.

FIG. 11 is a schematic illustrating peer networks, according to exemplary embodiments. FIG. 11 illustrates a peer-to-peer network architecture that also notifies of health events. Here the client device 22 may also directly communicate with one or more peer devices 150 via a personal area network 152. The personal area network 152 permits wireless, on-demand, direct communication links with the peer devices 150 in the vicinity of the client device 22. The personal area network 152, for example, may be a WI-FI or BLUETOOTH network that utilizes the Industrial, Scientific, and Medical band (2.4 GHz) of the frequency spectrum to provide short-range communication with the peer devices 150. WI-FI® and BLUETOOTH® are governed by the IEEE 802 family of standards for wireless communication over short ranges.

FIG. 11 illustrates an ad hoc nature of the personal area network 152. The client device 22 may have a wireless transmitter/receiver 154 ("TX/RX") that wirelessly communicates with the one or more peer devices 150. As the client device 22 encounters or discovers a peer device 150, the client-side health application 28 may invoke or call a peer module 156. The peer module 156 may be additional software code or instructions that cause the client device 22 to wirelessly query the peer device 150 for anonymous health information 156. The anonymous health information 156 describes any health-related data that is available from the peer device 150. The anonymous health information 156, for example, may describe weather, allergens, illness, diseases, and/or any other data available from the peer device 150. If the peer device 150 also stores and executes the client-side health application 28, then the devices 22 and 150 may handshake and authorize transmission of data. The peer module 156 instructs the client device 22 (such as the processor 92 illustrated in FIG. 2) to interface with the wireless transmitter/receiver 154 to retrieve the anonymous health information 156 from each peer device 150. The peer module 156 then instructs the processor 92 to store the anonymous health information 156 in a local health database 158. The local health database 46 is stored in the local memory (illustrated as reference numeral 94 in FIG. 2) of the client device 22.

The anonymous health information 156 is preferably anonymous. Because the peer devices 150 share their respective health data, many people may not want their personal information shared. Before any health data is retrieved and shared, then, exemplary embodiments may partially or completely anonymize the health data. Names, addresses, social security number, and other identifying information may be redacted or deleted.

Figure 12:
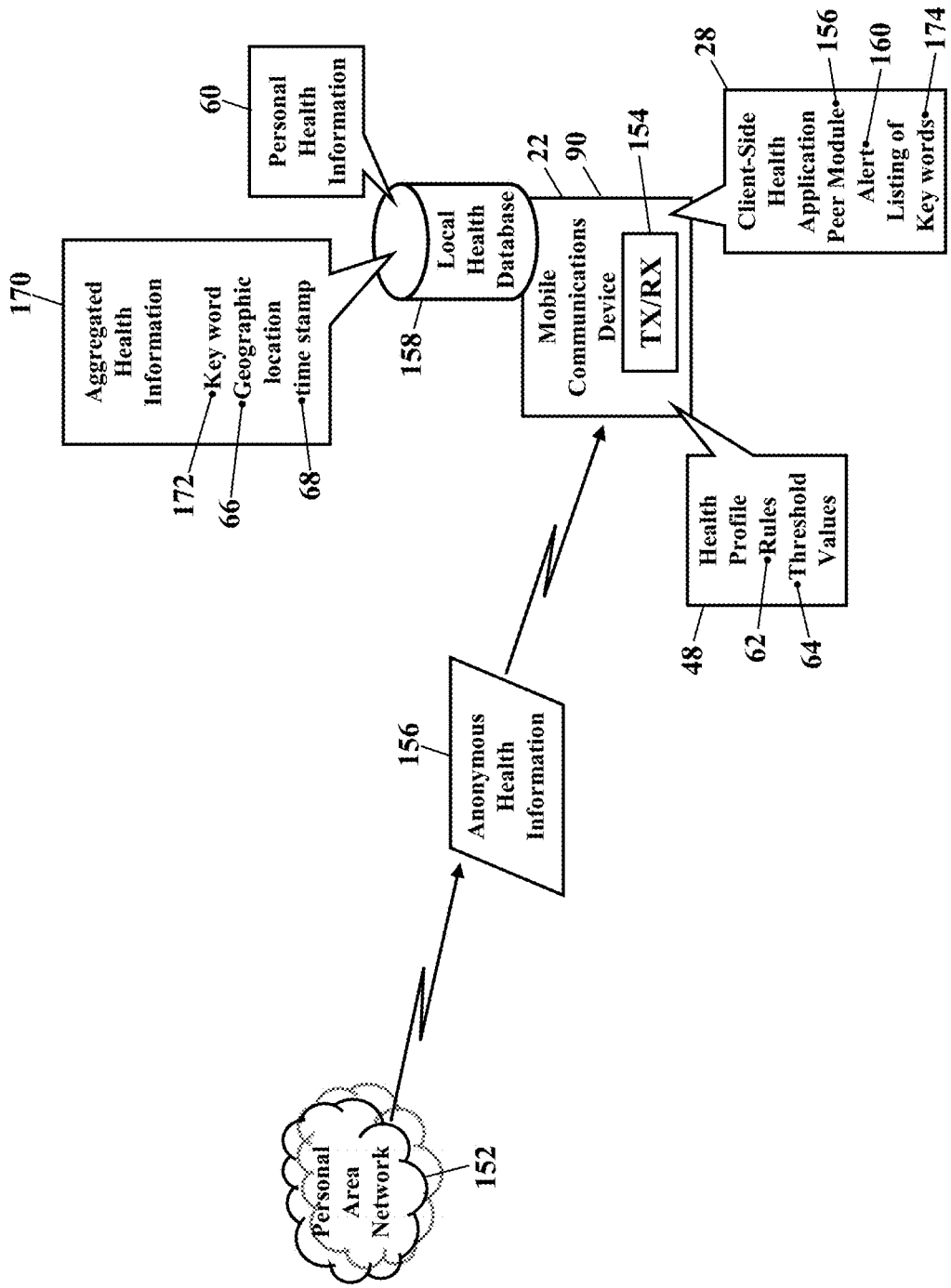
FIG. 12 is a schematic illustrating local processing, according to exemplary embodiments.

FIG. 12 is a schematic illustrating local processing, according to exemplary embodiments. Once the client device 22 (such as the mobile communications device 90) receives the anonymous health information 156, comparisons may then be made. As FIG. 12 illustrates, the client device 22 may locally store the health profile 48 in the local memory (illustrated as reference numeral 94 in FIG. 2). The peer module 156 compares the anonymous health information 156 to the health profile 48. As earlier paragraphs explained, the health profile 48 may also be locally stored in the memory 94 of the client device 22. The health profile 48 also stores the configurable rules 62 and the threshold values 64 for any health factors, parameters, or conditions of interest or concern. As the anonymous health information 156 is compared to the rules 62, the peer module 156 produces an alert 160 when any of the threshold values 64 are equaled or exceeded. The alert 160 visually and/or audibly informs the user of the client device 22 of some health event that may affect or impair the health of the user. Here, then, the user of the client device 22 may be visually and/or audibly alerted to health concerns derived from a complete stranger's anonymous health information 156 encountered in coffee shops, train/subway stations, restaurants, and other micro-environments.

FIG. 12 illustrates another comparison. Here the client device 22 may also compare the personal health information 60 to the rules 62 and to the threshold values 64. As earlier paragraphs explained, the health profile 48 may store the personal health information 60 related to the user of the client device 22. The personal health information 60 may include allergens, illnesses, medical concerns, blood type, height, weight, medical history, and even DNA/RNA markers. The personal health information 60 may include prescription medications, over-the-counter medications, alcohol consumption, and even illicit or illegal drugs. The personal health information 60 may include dietary habits, dietary restrictions, and physical limitations. The personal health information 60 may also include mental health parameters. As the personal health information 60 is compared to the rules 62, the peer module 156 produces the alert 160 when any of the threshold values 64 are equaled or exceeded. Here, then, the user of the client device 22 is alert when his or her own personal health information 60 is of concern.

FIG. 12 also illustrates aggregated health information 170. When the client device 22 receives the anonymous health information 156, the peer module 156 of the client-side health application 28 may aggregate the anonymous health information 156 with the personal health information 60 to produce the aggregated health information 170. The anonymous health information 156 and the personal health information 60 may be aggregated according to keywords 172, the geographic location 66, and/or the time stamp 68. The client-side health application 28, for example, may search the anonymous health information 156 and the personal health information 60 for a configurable listing 174 of keywords. The listing 174 of keywords may be selected from a menu by the user of the client device 22, or the keywords 172 may be defined by the user. Regardless, the client-side health application 28 may aggregate any of the anonymous health information 156 and the personal health information 60 that shares a common keyword 172 in the listing 174 of keywords. Likewise, the client-side health application 28 may aggregate any of the anonymous health information 156 and the personal health information 60 that shares a common geographic location 66 and/or that shares a common time stamp 68. Even though the aggregated health information 170 is produced, though, the anonymous health information 156 and the personal health information 60 may still be stored in the local health database 158 as separate data sets.

Figure 13:
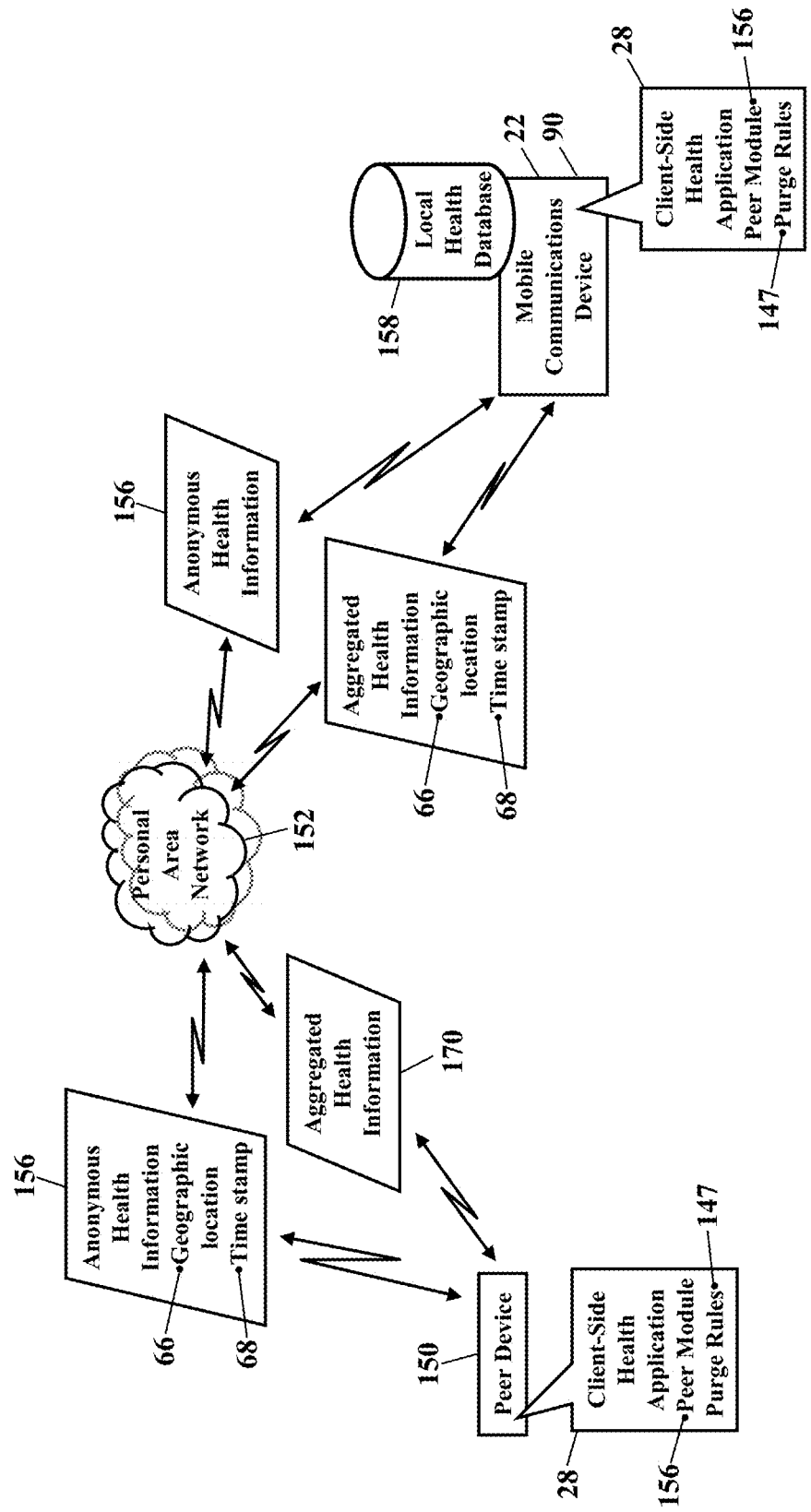
FIG. 13 is a schematic illustrating a personal area network, according to exemplary embodiments.

FIG. 13 is another schematic illustrating the personal area network 152, according to exemplary embodiments. Here the client device 22 and/or the peer device 150 may share their respective anonymous health information 156 and/or the aggregated health information 170. When both the client device 22 and the peer device 150 store and execute the peer module 156 of the client-side health application 28, then both devices 22 and 150 may exchange or swap their respective anonymous health information 156 and the aggregated health information 170. When both devices 22 and 150 wirelessly discover each other (via the personal area network 152), the client device 22 and the proximate peer device 150 exchange each other's locally stored information 156 and/or 170 via communications links and messages using the WIFI® or BLUETOOTH® standard. Each device 22 and 150 also sends or swaps the geographic location 66 and the time stamp 68 associated with each entry. Again, then, the client device 22 may retrieve the information 156 and/or 170 from peer devices 150 found in theaters, stores, parks, and other public/private spaces.

FIG. 13 also illustrates the purge rules 147. Because the client device 22 may store the personal health information 60, the anonymous health information 156, and/or the aggregated health information 170, the memory and processing requirement may be burdensome. As earlier paragraphs explained, then, exemplary embodiments may delete or purge information that is stale and/or no longer useful. The client-side health application 28, then, may compare the personal health information 60, the anonymous health information 156, and/or the aggregated health information 170 to the purge rules 147. That is, the client-side health application 28 may compare the geographic location 66 and the time stamp 68 associated with each entry to the purge rules 147. If any purge rule 147 is satisfied, then the corresponding entry is deleted from the local memory of the client device 22.

Figure 14:
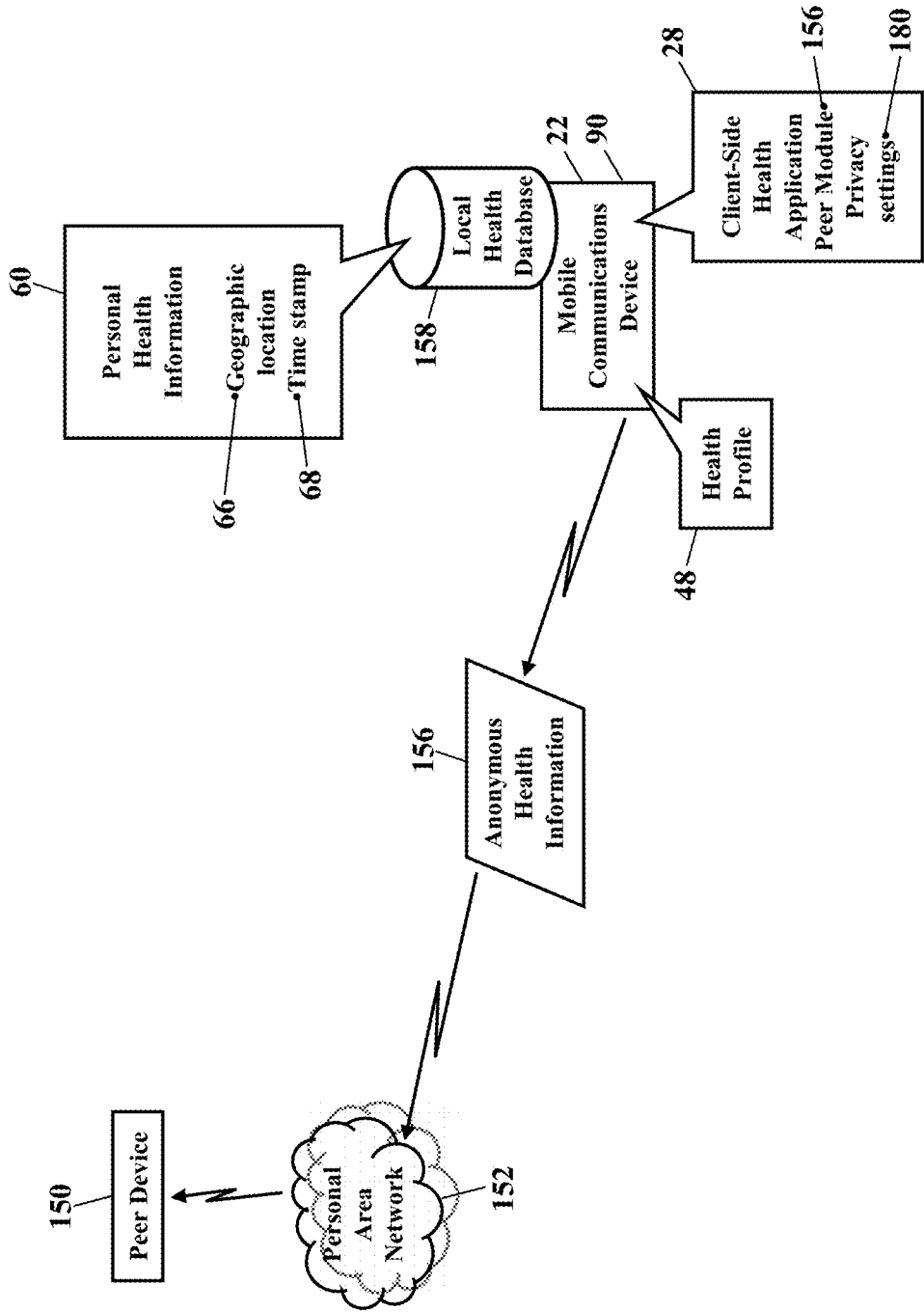
FIG. 14 is a schematic illustrating privacy settings, according to exemplary embodiments.

FIG. 14 is a schematic illustrating privacy settings, according to exemplary embodiments. As an above paragraph explained, some people may not want their personal information shared with the peer devices 150. Before the personal health information 60 is retrieved and sent, then, exemplary embodiments may partially or completely anonymize the personal health information 60. The peer module 156 of the client-side health application 28 may optionally have privacy settings 180 that prohibit certain information or data fields from being shared with the peer devices 150. Again, name(s) and address(es) may be prohibited from being retrieved and sent to the peer device 150. Telephone numbers and even Internet Protocol addresses may also be prohibited. Configuration settings may even be established to ensure certain information (such as ailments, diseases, or medications) are not revealed.

Figure 15:
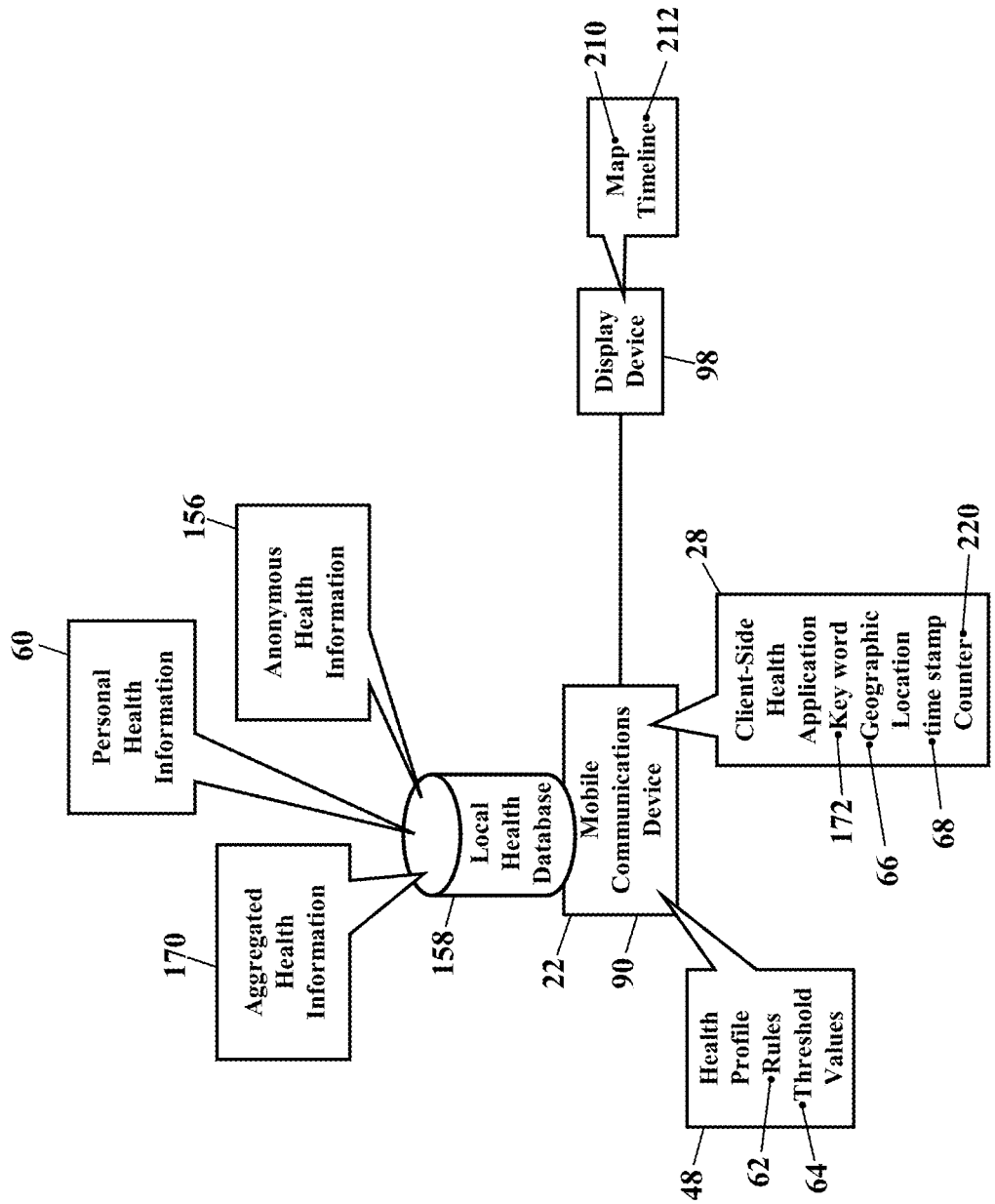
FIG. 15 is a schematic illustrating graphical outputs, according to exemplary embodiments.

FIG. 15 is a schematic illustrating graphical outputs, according to exemplary embodiments. Here exemplary embodiments may generate a geographic map 210 of any health events in the local health database 158. The user, for example, may first select a dataset to map. Because the local health database 158 stores the personal health information 60, the anonymous health information 156, and the aggregated health information 170, the user may first select which dataset to map. The client-side health application 28, for example, may have a drop-down menu or other means for selecting between the personal health information 60, the anonymous health information 156, and the aggregated health information 170. The user places a cursor on the desired dataset and makes a selection. The user may then instruct the client-side health application 28 to plot the selected dataset according to the geographic location 66. The client-side health application 28, for example, may plot the anonymous health information 156 according to the city, state, or country. The map 210 may be visually produced on the display device 98 and/or saved as a file. The personal health information 60 may, likewise, be plotted or overlaid onto the same map 210, thus visually illustrating the user's historical locations in relation to a peer's health events.

Exemplary embodiments also include timelines. Sometimes a time-based visual representation yields a better understanding of the data. Exemplary embodiments, then, also include an option to plot health events according to time. Again, the user selects a dataset to analyze (e.g., the personal health information 60, the anonymous health information 156, or the aggregated health information 170). The user then instructs the client-side health application 28 to chronologically arrange the dataset according to the time stamps 68. The client-side health application 28, for example, may plot the aggregated health information 170 according to date and time. The resultant health event timeline 212 may be visually produced on the display device 98 and/or saved as a file. The selected dataset may also be plotted according to the geographical location 66, thus illustrating a chronological and geographical reply of the dataset.

Datasets may also be filtered. Exemplary embodiments also include options to filter or sort the selected dataset according to the key words 172, the rules 60, and/or the threshold values 62. The user, for example, may want to only view a map of health events related to whooping cough. The user thus instructs the client-side health application 28 to search the selected dataset for "whooping cough" or other related keywords 172. The user may further sort the search results by the geographic location 66, thus revealing regional or local instances. Likewise, the user may search the selected database for the keyword 172 "mononucleosis" or some other pathogen. Searching and sorting techniques may be text-based or speech-based (wherein speech may be converted to text). Exemplary embodiments thus permit reducing the selected dataset to manageable and revealing samples using search and filter criteria.

Exemplary embodiments may also filter by the rules 60. Exemplary embodiments permit the user to create the logical rules 60 by which the selected dataset may be narrowed. Suppose, for example, that the user is only interested viral infections that exceed five hundred (500) events. The user, in other words, is not interested in very low occurrences. The user, then, may filter the selected dataset for the chosen keyword(s) 172, and the user may establish a counter 220. As the selected dataset is searched, the client-side health application 28 increments the counter 220 from an initial value (e.g., zero) when each keyword is matched. The client-side health application 28 compares a current value of the counter 220 to the threshold value 62 of the counter (500 in this example). Exemplary embodiments will thus only report the keyword 172 matches that exceed 500 counts. The counter 220 thus acts as another filtering mechanism to narrow the selected dataset.

Figure 16:
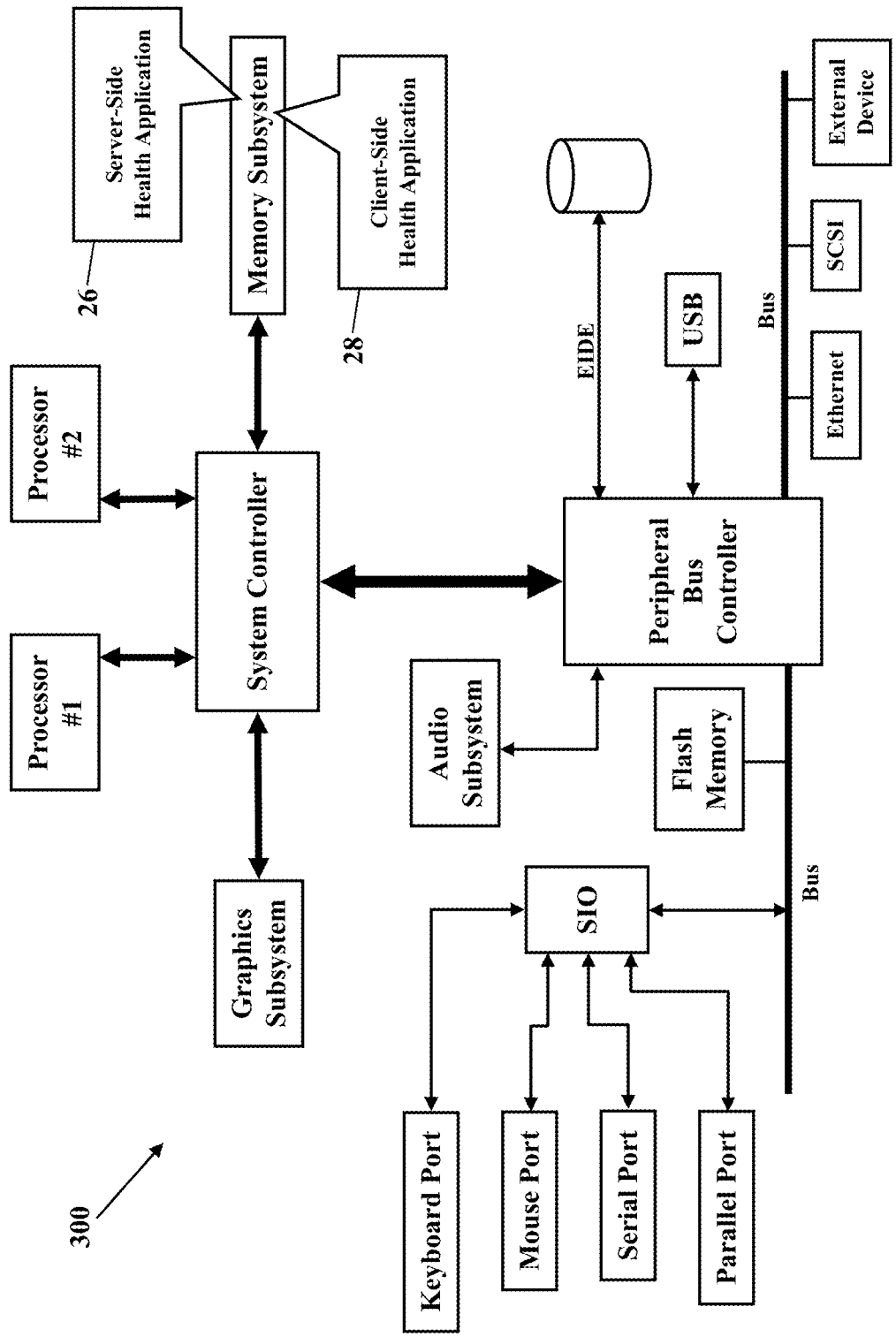
FIG. 16 depicts other possible operating environments for additional aspects of the exemplary embodiments.

FIG. 16 is a schematic illustrating still more exemplary embodiments. FIG. 16 is a generic block diagram illustrating the server-side health application 26 and the client-side health application 28 operating within a processor-controlled device 300. As the paragraphs explained, server-side health application 26 and the client-side health application 28 may operate in any processor-controlled device 300. FIG. 16, then, illustrates the server-side health application 26 and the client-side health application 28 stored in a memory subsystem of the processor-controlled device 300. One or more processors communicate with the memory subsystem and execute the server-side health application 26 and the client-side health application 28. Because the processor-controlled device 300 illustrated in FIG. 16 is well-known to those of ordinary skill in the art, no detailed explanation is needed.

Exemplary embodiments may be physically embodied on or in a computer-readable storage medium. This computer-readable medium may include CD-ROM, DVD, tape, cassette, floppy disk, memory card, flash memory, large-capacity disks, or any other physical storage medium. This computer-readable medium, or media, could be distributed to end-subscribers, licensees, and assignees. A computer program product comprises the computer read medium storing processor-executable instructions for notifying of health events, as explained above.

While the exemplary embodiments have been described with respect to various features, aspects, and embodiments, those skilled and unskilled in the art will recognize the exemplary embodiments are not so limited. Other variations, modifications, and alternative embodiments may be made without departing from the spirit and scope of the exemplary embodiments.

The invention claimed is:

1. A method, comprising:
   sending, by a mobile device, a request for a health information to a different mobile device, the request for the health information specifying a keyword;
   receiving, by the mobile device, the health information from the different mobile device, the health information associated with the keyword;
   receiving, by the mobile device, a location reported by the different mobile device;
   in response to the location reported by the different mobile device exceeding a threshold location, determining, by the mobile device, an irrelevancy of the health information; and
   purging, by the mobile device, the health information from a hardware memory device by executing a logical rule in response to the irrelevancy of the health information.

2. The method of claim 1, further comprising comparing the location to the threshold location.

3. The method of claim 1, further comprising determining a time associated with the health information received from the different mobile device.

4. The method of claim 3, further comprising:
   comparing the time associated with the health information to a threshold age; and
   determining that the health information received from the different mobile device exceeds the threshold age.

5. The method of claim 1, further comprising generating a notification in response to the health information received from the different mobile device.

6. The method of claim 1, further comprising determining a network access point associated with a communications network.

7. The method of claim 1, further comprising determining a network address associated with a network access point associated with a communications network.

8. A system, comprising:
   a hardware processor; and
   a memory device, the memory device storing instructions, the instructions when executed causing the hardware processor to perform operations, the operations comprising:
   sending a request for a health information to a mobile device, the request for the information specifying a keyword;
   receiving the health information from the mobile device that is associated with the keyword;
   receiving a location reported by the mobile device;
   comparing the location reported by the mobile device to a threshold location;
   in response to the location satisfying the threshold location, determining the health information received from the mobile device is relevant and aggregating the health information in a database;
   in response to the location failing to satisfy the threshold location, determining the health information received from the mobile device is irrelevant; and
   in response to the health information being irrelevant, executing a logical rule that causes the hardware processor to purge the health information from the memory device.

9. The system of claim 8, wherein the operations further comprise comparing a global positioning system information to the threshold location.

10. The system of claim 8, wherein the operations further comprise determining a time associated with the health information.

11. The system of claim 10, wherein the operations further comprise:
    comparing the time associated with the health information to a threshold age; and in response to the time exceeding the threshold age, determining that the health information is irrelevant.

12. The system of claim 8, wherein the operations further comprise generating a notification in response to the health information.

13. The system of claim 8, wherein the operations further comprise determining a network access point associated with a communications network.

14. The system of claim 8, wherein the operations further comprise determining a network address associated with a network access point.

15. A storage device storing computer program instructions which, when executed on a hardware processor, cause the hardware processor to perform operations, the operations comprising:
   sending a request for a health information to a mobile device, the request for the health information specifying a keyword;
   receiving the health information from the mobile device that is associated with the keyword;
   receiving a location reported by the mobile device;
   comparing the location reported by the mobile device to a threshold location;
   in response to the location satisfying the threshold location, determining the health information received from the mobile device is relevant and producing an aggregated health information by aggregating the health information associated with the keyword with a stored information also associated with the keyword;
   in response to the location failing to satisfy the threshold location, determining the health information received from the mobile device is irrelevant; and
   in response to the health information being irrelevant, retrieving and executing a logical rule that purges the health information.

16. The storage device of claim 15, wherein the operations further comprise comparing a global positioning system information to the threshold location.

17. The storage device of claim 15, wherein the operations further comprise determining a time associated with the health information.

18. The storage device of claim 17, wherein the operations further comprise:
   comparing the time associated with the health information to a threshold age; and
   in response to the time exceeding the threshold age, determining that the health information is irrelevant.

19. The storage device of claim 15, wherein the operations further comprise generating a notification in response to the health information.

20. The storage device of claim 15, wherein the operations further comprise determining a network access point associated with a communications network.

* * * * *